US00PP10297P

United States Patent [19]

Whitcomb

[11] Patent Number: Plant 10,297

[45] Date of Patent: Mar. 24, 1998

[54] CRAPE MYRTLE SHRUB NAMED 'WHIT I'

[76] Inventor: Carl E. Whitcomb, P.O. Box 2383, Stillwater, Okla. 74076

[21] Appl. No.: 732,779

[22] Filed: Oct. 14, 1996

[51] Int. Cl.[6] ..... A01H 5/00

[52] U.S. Cl. ..... Plt./67.3

[58] Field of Search ..... Plt./67.3

[56] References Cited

U.S. PATENT DOCUMENTS

| | | | |
|---|---|---|---|
| P.P. 4,182 | 1/1978 | Chopin | Plt./54 |
| P.P. 4,183 | 1/1978 | Chopin | Plt./54 |
| P.P. 4,184 | 1/1978 | Chopin | Plt./54 |
| P.P. 4,185 | 1/1978 | Chopin | Plt./54 |
| P.P. 5,302 | 10/1984 | Chopin | Plt./54 |
| P.P. 6,365 | 11/1988 | Whitcomb | Plt./54 |

*Primary Examiner*—James R. Feyrer
*Assistant Examiner*—Elizabeth C. Kemmerer
*Attorney, Agent, or Firm*—Bill D. McCarthy; Phillip L. Free, Jr.; Randall K. McCarthy

[57] ABSTRACT

A new and distinct variety of crape myrtly, *Lagerstroemia indica*, which is characterized by a dense, upright, and pyramidal growth habit, leathery leaves which emerge crimson and slowly change to medium green, few seed heads, late flowering season, inflorescences which are six to twelve inches tall and four to eight inches wide, and flower petals that range from cardinal red bordered irregularly by white on hot summer days to pink with more white on cooler or cloudy days.

2 Drawing Sheets

BACKGROUND OF THE INVENTION

1. Field of the Invention

The present invention relates to a new and distinct variety of cultivar of the ornamental shrub, *Lagerstroemia indica*, commonly known as crape myrtle.

2. Description of the Prior Art

The crape myrtle shrub is native to eastern China and was introduced into North America in the late 1700s. Since then this popular ornamental shrub has been grown extensively throughout the continent. Over the years, seedlings and hybrids between *L. indicia* and *L. fauriei*, have been selected for various growth forms, flower colors, or other features and propagated asexually. As assortment of methods have been utilized in attempting to develop improved varieties of crape myrtles, at least several of which have had U.S. Plant Patents issued.

For example, U.S. Plant Pat. No. 4,182, U.S. Plant Pat. No. 4,183, U.S. Plant Pat. No. 4,184 and U.S. Plant Pat. No. 4,185 disclose and claim a series of four new varieties of *Lagerstroemia indicia* produced by crossing previously-known varieties. Each of these new varieties was characterized as having a weeping growth habit at maturity. U.S. Plant Pat. No. 5,302 also discloses a new variety of crape myrtle exhibiting a weeping growth habit at maturity.

U.S. Plant Pat. No. 6,365 discloses a variety of crape myrtle derived from seedlings that had been treated with a mutation inducing chemical. The plant was characterized as having variegated pink-flowers bordered by pure white and flowering over an extremely long period of time.

It is generally known that ethyl methane sulfonic acid methyl ester, EMS, is capable of producing plant mutations. EMS sometimes induces partial or complete sterility in the mutant plant and the mutants often have thicker than normal leaves and variegated flowers, with an occasional flower that is a solid color among the predominantly variegated flowers. The new variety of crape myrtle of the present may be such a mutant.

SUMMARY OF THE INVENTION

The present invention involves the discovery of a new and distinct variety of crape myrtle, *Lagerstroemia indica*, which is characterized by a dense, upright, and pyramidal growth habit, large shrub or small tree that may reach 15 feet in height. The leaves of the plant emerge crimson and slowly change to medium green and are more leathery than the species average. Inflorescences are six to 12 inches tall and four to eight inches wide. Individual petals are cardinal red bordered irregularly by white. During hot summer days the flowers will be cardinal red and contain little white, whereas during cooler and/or cloudy days, the flowers will be less red, nearly pink, and have more white. Flowering generally begins later in the season than with other crape myrtle varieties, mid August in north central Oklahoma, but flowering continues until frost. Few seed heads are produced which further enhances the prolonged flowering.

BRIEF DESCRIPTION OF THE DRAWINGS

FIG. 1 is a photographic view of my new crape myrtle shrub in full color showing the general form and arrangement of a typical plant that has had the central stem removed.

FIG. 2 is a photographic view in full color of the maturing foliage of the shrub of FIG. 1, showing the new growth and the progression of color change as the leaves age.

FIG. 3 is a photographic view in full color of flowers of the shrub of FIG. 1, showing the variation in flower color.

DESCRIPTION OF THE VARIETY

The new variety of crape myrtle, which has been given the cultivar name "Whit I," was selected from over 65,000 seedlings grown from a seedling parent that had been selected because of the dark foliage and near red flowers and produced large quantities of seeds with good germination and seedling vigor. Prior to planting, the seeds were treated with ethylmethane sulfonic acid methyl ester, EMS, which is generally known to be capable of producing plant mutations. Treated seeds were planted in flats in the greenhouse. After the seeds germinated, the seedlings were transplanted into small containers and mildew was introduced from susceptible seedlings in large containers. Seedlings susceptible to mildew or with poor vigor were rogued out and the remainder of the seedlings were planted in rows in an open field for further evaluation. The new variety was selected from the population in the field for the unique foliage color, growth form, and flower color. It s probably a mutant arising from the EMS treatment. EMS is known to induce sterility. Mutant plants resulting from EMS treatments often have thicker than normal leaves with variegated flowers with an occasional flower that is solid color among the predominantly variegated flowers. Such characteristics have been observed in this new variety of crape myrtle.

Softwood cuttings taken from the original parent have been successfully rooted in a medium of peat and perlite under intermittent mist in Oklahoma. Subsequent cuttings taken from plants resulting from previous cuttings have been similarly rooted. Growth, flowering, and flower and foliage color remain consistent with the parent. The plant does not reproduce from seed.

A detailed description of the new variety of crape myrtle follows:

Parentage: Selected from over 65,000 crape myrtle seedlings grown from a selected seedling parent. The seeds were treated with EMS to induce mutations. The thick leathery leaves, variegated flowers, long bloom time, and near sterility are indication that the new variety is a mutant.

Growth: The plant is a vigorous upright grower in pyramidal form when young but spreads at the crown with age. Height with age may reach 15 feet or more. Vegetative growth is rapid in spring and continues until mid summer when flowering begins. Only modest growth occurs after flowering begins. Unlike most crape myrtle which produce many vertical stems of similar vigor, this new crape myrtle produces a vigorous growing central stem with many side branches, thus creating the pyramidal form. If the central stem is cut or killed, than a proliferation of upright stems result as shown in FIG. 1.

Foliage: Leaves are similar in size to the species average, but are more thick and leathery and with excellent retention. New leaves emerge crimson (FIG. 2), Grayed-purple Group 185-A and CIE coordinates 0.519, 0.312, 8.5 (color notations from The Royal Horticulture Society Colour Chart, 1966 and the Commission International de l'Esclairage 1931) and gradually change to medium green, Green Group 137-A (R.H.S.) and CIE 0.325, 0.419, 10.0. The color varies with light intensity and growing conditions. Foliage has been very resistant to powdery mildew in test in Florida and Texas and Oklahoma, but some mildew did occur in late fall in northern Alabama.

Flowers: Individual petals are cardinal red in full sun (FIG. 3), Red Group 53-B (R.H.S.) and CIE 0.522, 0.298, 8.3 with a white margin, White Group 155-B (R.H.S.) and CIE 0.320, 0.333, 88.9. The width and presence of the white and presence of the white margin varies with temperature, light intensity, and growing conditions, but is generally present in an inflorescence. As the flowers age they generally fall cleanly from the inflorescence without discoloring and becoming unattractive. Unopened flower buds are crimson, Grayed-purple Group 185-A (R.H.S.) and CIE 0.519, 0.312, 8.5. The new variety generally begins flowering in early to mid August and continues into October. This period is longer than most seedlings and cultivars of crape myrtle. Flowering continues during drought or periods of prolonged heat. Seed set is nonexistent or very light which accounts for the extended flowering.

Cold hardiness: The new variety of crape myrtle has withstood temperatures of −5° F., −2° F. and 0° F. with no injury. The top of the plant was killed to the soil line at −13° F., but quickly regrew the following spring and flowered in summer.

I claim:

1. A new and distinct variety of *Lagerstroemia indica*, crape myrtle, plant substantially as shown and described and partially characterized by a dense, upright, and pyramidal growth habit large shrub or small tree that may reach 15 feet or more in height, crimson new leathery foliage that quickly changes to medium green with age, a variegated flower predominantly cardinal red bordered by white on the outer margin, few seeds, and an exceptionally long bloom period.

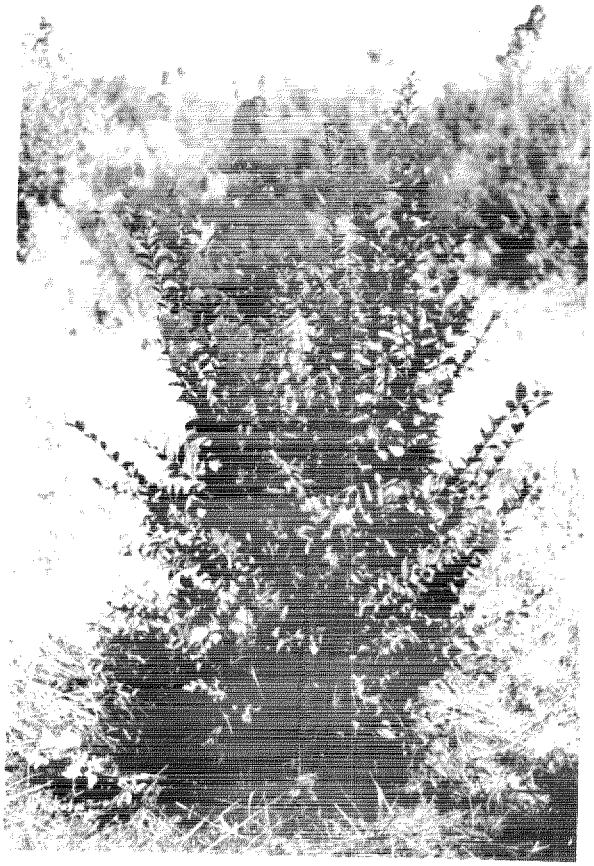

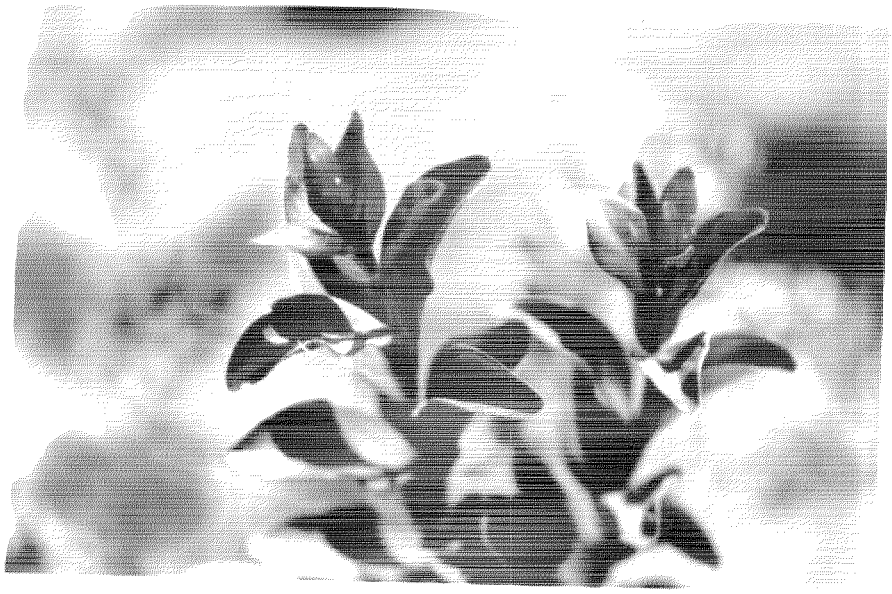
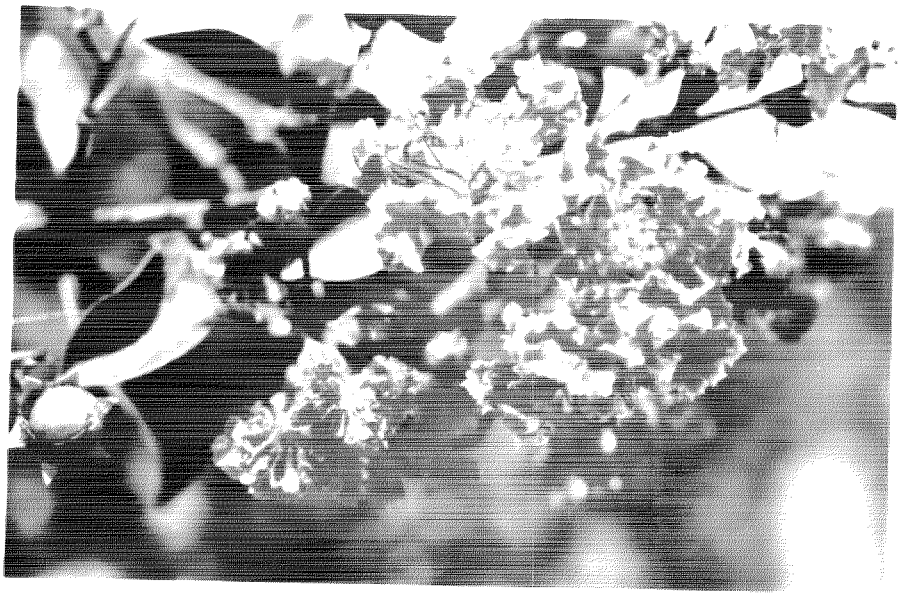

* * * * *